US009343654B2

(12) United States Patent
Moore et al.

(10) Patent No.: US 9,343,654 B2
(45) Date of Patent: May 17, 2016

(54) METHOD OF MANUFACTURING IMPLANTABLE WIRELESS ACOUSTIC STIMULATORS WITH HIGH ENERGY CONVERSION EFFICIENCIES

(71) Applicant: EBR Systems, Inc., Sunnyvale, CA (US)

(72) Inventors: David F. Moore, San Carlos, CA (US); Paul Mohr, Aptos, CA (US); N. Parker Willis, Atherton, CA (US); Axel F. Brisken, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 14/883,925

(22) Filed: Oct. 15, 2015

(65) Prior Publication Data
US 2016/0035967 A1 Feb. 4, 2016

Related U.S. Application Data

(60) Division of application No. 14/059,228, filed on Oct. 21, 2013, now Pat. No. 9,180,285, which is a division of application No. 13/734,680, filed on Jan. 4, 2013, now Pat. No. 8,588,926, which is a continuation-in-part of application No. 12/721,483, filed on Mar. 10, 2010, now Pat. No. 8,364,276, which is a continuation-in-part of application No. PCT/US2009/038258, filed on Mar. 25, 2009.

(60) Provisional application No. 61/039,340, filed on Mar. 25, 2008.

(51) Int. Cl.
*A61N 1/375* (2006.01)
*H01L 41/25* (2013.01)
*A61N 1/378* (2006.01)

(52) U.S. Cl.
CPC .............. *H01L 41/25* (2013.01); *A61N 1/3758* (2013.01); *A61N 1/3787* (2013.01)

(58) Field of Classification Search
None
See application file for complete search history.

(56) References Cited

U.S. PATENT DOCUMENTS 3,659,615 A 5/1972 Enger
3,735,756 A 5/1973 Richards et al.
(Continued)

FOREIGN PATENT DOCUMENTS

DE 4330680 A1 3/1995
GB 1146976 A 3/1969
(Continued)

OTHER PUBLICATIONS

European office action dated Apr. 13, 2012 for Application No. 09725884.2.
(Continued)

*Primary Examiner* — Kennedy Schaetzle
(74) *Attorney, Agent, or Firm* — Wilson Sonsini Goodrich & Rosati

(57) ABSTRACT

Receiver-stimulator with folded or rolled up assembly of piezoelectric components, causing the receiver-stimulator to operate with a high degree of isotropy are disclosed. The receiver-stimulator comprises piezoelectric components, rectifier circuitry, and at least two stimulation electrodes. Isotropy allows the receiver-stimulator to be implanted with less concern regarding the orientation relative the transmitted acoustic field from an acoustic energy source.

6 Claims, 21 Drawing Sheets

(56) References Cited

U.S. PATENT DOCUMENTS

| | | |
|---|---|---|
| 3,767,971 A | 10/1973 | Patrick |
| 4,050,004 A | 9/1977 | Greatbatch |
| 5,193,539 A | 3/1993 | Schulman et al. |
| 5,266,746 A | 11/1993 | Nishihara et al. |
| 5,314,453 A | 5/1994 | Jeutter |
| 5,749,909 A | 5/1998 | Schroeppel et al. |
| 5,833,710 A | 11/1998 | Jacobson |
| 6,140,740 A | 10/2000 | Porat et al. |
| 6,504,286 B1 | 1/2003 | Porat et al. |
| 6,628,989 B1 | 9/2003 | Penner et al. |
| 6,654,638 B1 | 11/2003 | Sweeney |
| 6,764,446 B2 | 7/2004 | Wolinsky et al. |
| 6,771,785 B2 | 8/2004 | Pompei |
| 7,283,874 B2 | 10/2007 | Penner |
| 7,489,967 B2 | 2/2009 | Von Arx et al. |
| 7,522,962 B1 | 4/2009 | Doron et al. |
| 7,542,804 B2 | 6/2009 | Mandell |
| 7,606,621 B2 | 10/2009 | Brisken et al. |
| 7,610,092 B2 | 10/2009 | Cowan et al. |
| 7,865,247 B2 | 1/2011 | Smith et al. |
| 7,983,748 B2 | 7/2011 | Ruse et al. |
| 8,364,276 B2 | 1/2013 | Willis |
| 8,588,926 B2 | 11/2013 | Moore et al. |
| 2002/0077673 A1 | 6/2002 | Penner et al. |
| 2003/0104269 A1 | 6/2003 | Gan et al. |
| 2004/0172083 A1 | 9/2004 | Penner |
| 2004/0204744 A1 | 10/2004 | Penner et al. |
| 2005/0154294 A1 | 7/2005 | Uchiyama et al. |
| 2005/0165456 A1 | 7/2005 | Mann et al. |
| 2006/0004424 A1 | 1/2006 | Loeb et al. |
| 2006/0136004 A1 | 6/2006 | Cowan et al. |
| 2006/0136005 A1 | 6/2006 | Brisken et al. |
| 2007/0027580 A1 | 2/2007 | Ligtenberg et al. |
| 2007/0055184 A1 | 3/2007 | Echt et al. |
| 2007/0167988 A1* | 7/2007 | Cernasov ............ H02N 11/002 607/35 |
| 2007/0233200 A1 | 10/2007 | Maschke |
| 2007/0282383 A1 | 12/2007 | Koyama |
| 2007/0293895 A1 | 12/2007 | Cowan et al. |
| 2008/0243210 A1 | 10/2008 | Doron et al. |
| 2008/0294208 A1 | 11/2008 | Willis et al. |
| 2008/0312720 A1 | 12/2008 | Tran et al. |
| 2010/0234924 A1 | 9/2010 | Willis |
| 2012/0203306 A1 | 8/2012 | Sarvazyan |
| 2013/0197609 A1 | 8/2013 | Moore et al. |
| 2013/0274828 A1 | 10/2013 | Willis |
| 2014/0046420 A1 | 2/2014 | Moore et al. |

FOREIGN PATENT DOCUMENTS

| | | |
|---|---|---|
| WO | WO-2005009535 A1 | 2/2005 |
| WO | WO-2007016581 A2 | 2/2007 |
| WO | WO-2007016581 A3 | 5/2007 |
| WO | WO-2007149936 A2 | 12/2007 |
| WO | WO-2007149936 A3 | 10/2008 |
| WO | WO-2009120785 A2 | 10/2009 |
| WO | WO-2009120785 A3 | 12/2009 |

OTHER PUBLICATIONS

European search report and opinion dated Jun. 27, 2011 for EP Application No. 09725884.2.

European search report and opinion dated Sep. 26, 2013 for EP Application No. 11754116.9.

European search report dated Apr. 18, 2012 for Application No. 12151794.0.

International search report and written opinion dated May 19, 2011 for PCT/US2011/027985.

International search report and written opinion dated May 25, 2009 for PCT/US2009/038258.

Notice of allowance dated Jul. 22, 2013 for U.S. Appl. No. 13/734,680.

Notice of allowance dated Jul. 31, 2015 for U.S. Appl. No. 14/059,228.

Notice of allowance dated Sep. 28, 2012 for U.S. Appl. No. 12/721,483.

Office action dated Jan. 12, 2015 for U.S. Appl. No. 14/059,228.

Office action dated Jun. 11, 2012 for U.S. Appl. No. 12/721,483.

Office action dated Jun. 13, 2014 for U.S. Appl. No. 13/648,027.

Office action dated Dec. 22, 2014 for U.S. Appl. No. 13/648,027.

* cited by examiner

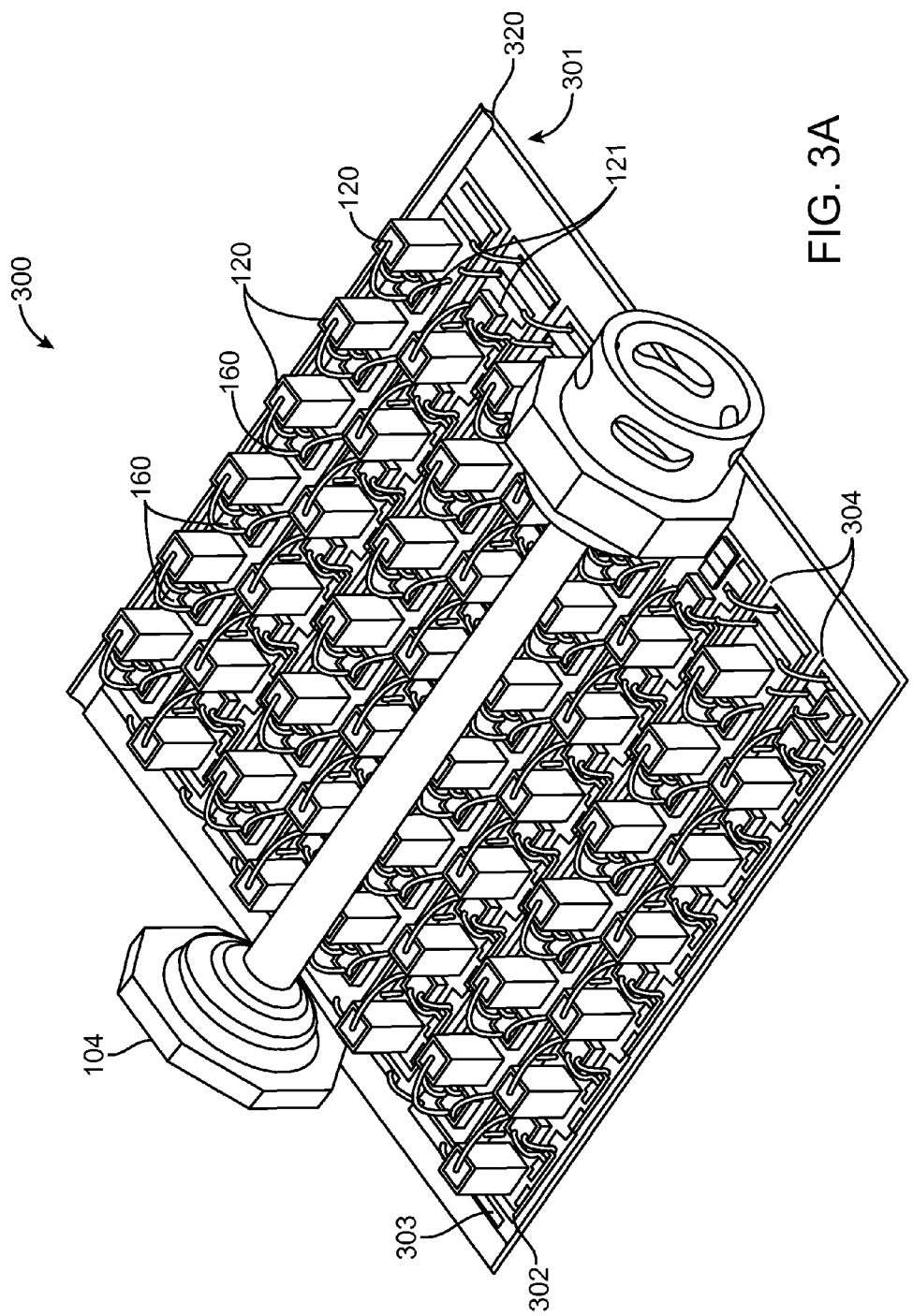

METHOD OF MANUFACTURING IMPLANTABLE WIRELESS ACOUSTIC STIMULATORS WITH HIGH ENERGY CONVERSION EFFICIENCIES

CROSS-REFERENCE TO RELATED APPLICATION

This application is a divisional of U.S. patent application Ser. No. 14/059,228 (now U.S. Pat. No. 9,180,285), filed Oct. 21, 2013, which is a divisional of U.S. patent application Ser. No. 13/734,680 (now U.S. Pat. No. 8,588,926), filed Jan. 4, 2013, which is a continuation-in-part of U.S. patent application Ser. No. 12/721,483 (now U.S. Pat. No. 8,364,276), filed Mar. 10, 2010, which is a continuation-in-part of International (PCT) Patent Application No. PCT/US2009/038258, filed Mar. 25, 2009, which claimed the benefit of U.S. Provisional Patent Application No. 61/039,340, filed on Mar. 25, 2008, the disclosures of which are incorporated herein by reference.

BACKGROUND OF THE INVENTION

1. Field of the Invention

The present invention relates to a wireless acoustic stimulation system for stimulating biological tissue and, in particular, for a receiver-stimulator that converts an acoustic field into electrical power at high energy conversion efficiency to deliver stimulation energy to tissue. The receiver-stimulator has highly isotropic performance based on the mechanical and electrical arrangement of multiple acoustic power harvesting elements in the receiver-stimulator unit.

2. Description of the Background Art

Stimulation of cardiac tissue using acoustic energy based systems comprising a controller-transmitter and one or more implanted receiver-stimulator devices has recently been proposed by the inventors of this patent application and described in detail, for example in published US Application Publication No. 2006/0136004. The controller-transmitter transmits acoustic energy by producing an acoustic field that is transmitted over time. The acoustic field is a propagating acoustic wave defined by its direction and its intensity (i.e., its power per unit area, typically expressed as Watts/meter$^2$). The acoustic field varies and attenuates as it propagates through the body due to absorption, refraction, and reflection. To minimize losses, the controller-transmitter focuses, or attempts to maximize, the acoustic field on the receiver-stimulator. In turn, the receiver-stimulator maximizes harvesting and converting of the acoustic field impinging upon it into electrical power delivered over time to the tissue to stimulate the tissue (stimulation energy). In general, this receiver-stimulator is a specialized transducer, that is, a device that converts acoustic power to electrical power. In another perspective the receiver-stimulator uses the converted power as a tissue stimulator that delivers electrical energy to cardiac or other tissue through tissue stimulation electrodes. The controller-transmitter may be applied externally on the body, but will usually be implanted in the body, requiring that the controller-transmitter have a reasonable size, similar to that of implantable pacemakers, and that the controller-transmitter be capable of operating from batteries for a lengthy period, typically three or more years. The relatively small size and relatively long operational period make it desirable that the receiver-stimulators harvest as much of the acoustic field transmitted by the controller-transmitter as possible. Furthermore, it is desirable to maximize the isotropy of the receiver-stimulator, whereby the electrical output power delivered to the tissue is constant or nearly constant as the receiver-stimulator's orientation is varied relative to the propagation direction of the acoustic field transmitted by the controller-transmitter, as this orientation is not always predictable.

Piezoelectric components, i.e., piezoelectric transducers, are typically used in acoustic applications to convert mechanical vibrations, such as in an acoustic field, to electrical power. They can also be used in the reverse to convert electrical power into a mechanical, vibrational wave, e.g., an acoustic wave. Coupling of mechanical vibrations in an acoustic field to piezoelectric transducers is an important consideration. The mechanical structure, or portions of the mechanical structure surrounding a piezoelectric component, which is exposed to the acoustic field determines the aperture, or surface, for coupling the acoustic field into the piezoelectric component. Generally, there is a tradeoff between aperture size/isotropy and the electrical power produced by an associated piezoelectric component. On the one hand a large aperture is desired to collect more acoustic power (and can then convert it to more electrical power). However, this comes at the expense of isotropy. The larger an aperture relative to the wavelength of the acoustic field it is placed in, the less isotropic it becomes. Therefore, a receiver-stimulator consisting of a single piezoelectric component is limited in its ability to produce high electrical output and exhibit high isotropy. It can either produce high electrical output power or high isotropy, but not both.

The piezoelectric components produce AC electrical power which is not optimized for tissue stimulation. A rectifier component is used to convert this electrical power to an electrical output which can be configured to effectively stimulate the tissue (e.g., into a DC output but other output waveforms are also effective). Furthermore, the AC electrical power produced by separate piezoelectric components can be out of phase, making it difficult to combine these outputs directly without loss of power. Rectifying these outputs prior to combining them reduces this power loss. Therefore, it would be advantageous to have one rectifier associated with each piezoelectric component. Furthermore, we can view the combination of a piezoelectric component, its associated aperture and rectifier as a single harvesting element that is capable of producing electrical power when placed in an acoustic field. The receiver-stimulator is then a collection of multiple harvesting elements whose electrical outputs are combined to deliver an electrical output to tissue in order to stimulate the tissue.

Once constructed, it is important to consider the assessment of the efficiency and isotropy of the entire receiver-stimulator rather than the individual harvesting elements. The Effective Area of the receiver-stimulator can be defined in terms of the electrical output power delivered to the tissue divided by the acoustic intensity (power/(power/meter$^2$)). Efficiency is then a measure of the Effective Area divided by the physical cross-sectional area of the receiver-stimulator that is exposed to an acoustic field. The Highest Efficiency then would be when the Effective Area approximates the physical cross-sectional area of the receiver-stimulator. To associate efficiency with isotropy, the aggregate performance over all possible orientations of the receiver-stimulator to the acoustic field must be considered. It would be desirable to have a receiver-stimulator that has high efficiency and a high degree of isotropy.

It would be desirable to provide implantable receiver-stimulator devices which are able to efficiently harvest power from an acoustic field transmitted from implanted or external acoustic transmitters and convert the acoustic power into stimulating electrical energy in an efficient manner. It would be particularly desirable if the receiver-stimulators could operate with a high degree of isotropy, where the electrical output power delivered to the tissue is constant or nearly constant as the receiver-stimulator's orientation is varied relative to the propagation direction of the acoustic field transmitted by the controller-transmitter, irrespective of whether the individual harvesting elements in the receiver-stimulator are themselves considered to be isotropic or non-isotropic. At least some of these objectives will be met by the inventions described hereinafter.

The following patents and patent publications describe various implantable transducers capable of converting applied acoustic waves into an electrical output: U.S. Pat. Nos. 3,659,615; 3,735,756; 5,193,539; 6,140,740; 6,504,286; 6,654,638; 6,628,989; and 6,764,446; U.S. Patent Application Publications 2002/0077673; 2004/0172083; and 2004/0204744; and published German application DE 4330680. U.S. Pat. No. 6,504,286 by Porat et al. describes a miniature piezoelectric transducer for providing maximal electric output when impinged by external acoustic waves in the low frequency range. The patent discloses various techniques including the aggregate mechanical structure of the device being omni-directional, changing the mechanical impedance of the piezoelectric layer, etc. As mentioned earlier, it would be desirable to have the receiver-stimulator itself be virtually isotropic rather than rely on the isotropy characteristics of the individual harvesting elements.

BRIEF SUMMARY OF THE INVENTION

Systems and methods are provided for delivering electrical energy to body tissues for many therapeutic indications. The electrical energy will typically be delivered in order to stimulate tissue, for example to stimulate cardiac tissue for therapeutically pacing the heart to treat bradycardia, for termination of tachyarrhythmia, for bi-ventricular resynchronization therapy for heart failure, or the like. The systems and methods of the present invention, however, could be used in a variety of other applications, including applications for nerve stimulation, brain stimulation, voluntary muscle stimulation, gastric stimulation, bone growth stimulation, pain amelioration, and the like.

In a first aspect, the present invention provides an implantable receiver-stimulator device which is capable of harvesting acoustic power from an acoustic field that is delivered from an acoustic source (physically separate from the receiver-stimulator device) and converting that acoustic power to electrical power to deliver electrical energy to stimulate tissue. The receiver-stimulator of the present invention is configured to be efficient, meaning it harvests all or nearly all of the acoustic power available and converts it into electrical power sufficient to stimulate cardiac tissue. In addition to efficient harvesting of acoustic power, the implantable receiver-stimulators of the present invention are also capable of functioning with a high degree of isotropy. This means that the output electrical power of the receiver-stimulator is constant or nearly constant as the receiver-stimulator's orientation is varied, relative to the propagation direction of the acoustic field transmitted by the controller-transmitter. In addition, the receiver-stimulator consists of multiple harvesting elements integrated into a mechanical structure that in aggregate provide high efficiency and a high degree of isotropy.

In a first specific embodiment, an implantable receiver-stimulator comprises a hermetically sealed enclosure with an inner and outer surface and a plurality of harvesting elements. Each harvesting element consists of a piezoelectric component with one face of the component affixed to the inner surface defining an aperture for coupling an acoustic field from the outer surface of the receiver-stimulator to the piezoelectric component and a rectifier circuit electrically connected to the output of the piezoelectric component that produces an electrical signal from each harvesting element. A mechanism is provided for combining the output of multiple harvesting elements to produce a biologically stimulating electrical output, such as output suitable for cardiac pacing, nerve stimulation, brain stimulation, voluntary muscle stimulation, pain amelioration, or the like. At least two electrodes in electrical contact with the tissue are coupled to the rectifier circuitry to receive the stimulating electrical output and deliver said output to tissue. Either or both of the stimulation electrodes may be mounted directly on the device, in some instances forming a portion of the device casing, or extend from the device.

One embodiment of the receiver-stimulator device is a hermetically sealed structure with an octagonal cross-section, optionally with an end cap at the proximal end of the longitudinal axis and another at the distal end. The device may also be shaped substantially cylindrically. The device has an inner and outer surface and is constructed using an electrically conductive base that is preferably biocompatible, such as titanium, upon which a circuit layer is built on the inner surface of the device. Additionally, a plurality of harvesting elements are organized on the inner surface of the device, creating multiple apertures for harvesting acoustic power from the outer surface of the receiver-stimulator. Each harvesting element consists of a piezoelectric component attached to its associated aperture and electric connections that are connected to its associated rectifier, with the piezoelectric element and the rectifier both mounted to the inner surface. The inner surface may also contain additional circuitry that combines the output power from each of the individual harvesting elements to the pair of electrodes that are in electrical contact with the tissue. The electrodes are located on the exterior surface of, or otherwise attached to or extended from, the receiver-stimulator device.

The proximal end of the receiver-stimulator can have mechanical or electromechanical arrangements to engage and disengage the receiver from a placement catheter. The distal end of the device has a retractable tissue engagement mechanism that enables the receiver-stimulator to be attached to a desired location at the treatment site. One of the stimulation electrodes may be part of the tissue engagement mechanism and the other stimulation electrode may be located on the exterior surface of the receiver-stimulator.

In another aspect of the present invention, methods for delivering acoustic power to an implanted receiver-stimulator comprise implanting a receiver-stimulator, typically formed as an assembly containing multiple harvesting elements, the receiver-stimulator having a high degree of isotropy as described above in connection with the devices of the present invention. An acoustic field is directed to the implanted receiver-stimulator assembly from an acoustic source, which may be implanted or located externally, and the receiver-stimulator outputs electrical power to tissue in proportion to the acoustic intensity impinging on the receiver-stimulator such that the minimum effective area is no more than −3 dB from the maximum effective area as the orientation of the receiver-stimulator varies relative to that of the acoustic source. With sufficient acoustic intensity the harvested acoustic power is converted to electrical power and is rectified by circuitry to produce a biologically stimulating electrical output, and the electrical output is delivered to tissue. The acoustic field may be delivered to the receiver-stimulator from an external source, but will preferably be delivered from an implanted acoustic source. The electrical output flowing over time between stimulation electrodes which are in electrical contact with tissue may possess specific characteristics of voltage, current, waveform, and the like. These electrical characteristics will be selected to stimulate the target cardiac tissue, nerve tissue, brain tissue, voluntary muscle tissue, bone tissue, or the like.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 3A shows a can assembly with piezoelectric components and rectifiers organized in an exemplary arrangement.

DETAILED DESCRIPTION OF THE INVENTION

In the following description, for purposes of explanation, numerous specific details are set forth in order to provide a thorough understanding of the invention. It will be apparent, however, to one skilled in the art that the invention can be practiced without these specific details.

In a first aspect, the present invention provides an implantable receiver-stimulator (hereinafter also abbreviated as "R-S" and also referred to as "stimulator") device which is capable of wirelessly harvesting acoustic power from an acoustic field delivered from an acoustic source physically separate from the R-S, and converting that acoustic power to electrical power, rectifying the electrical power, and delivering an electrical output between two stimulation electrodes.

Figure 1A:
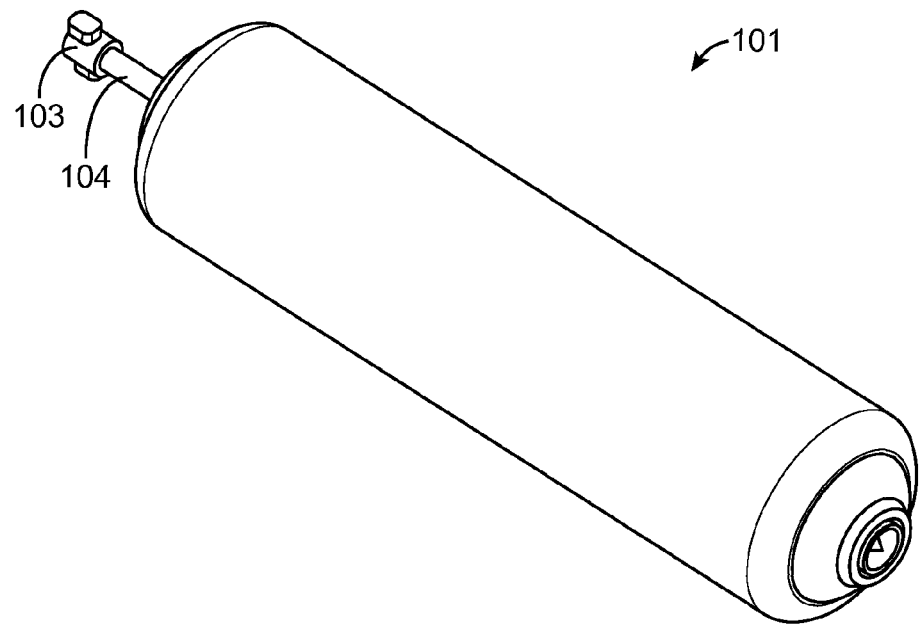
FIG. 1A shows a receiver-stimulator with the anchoring mechanism retracted.
Figure 1B:
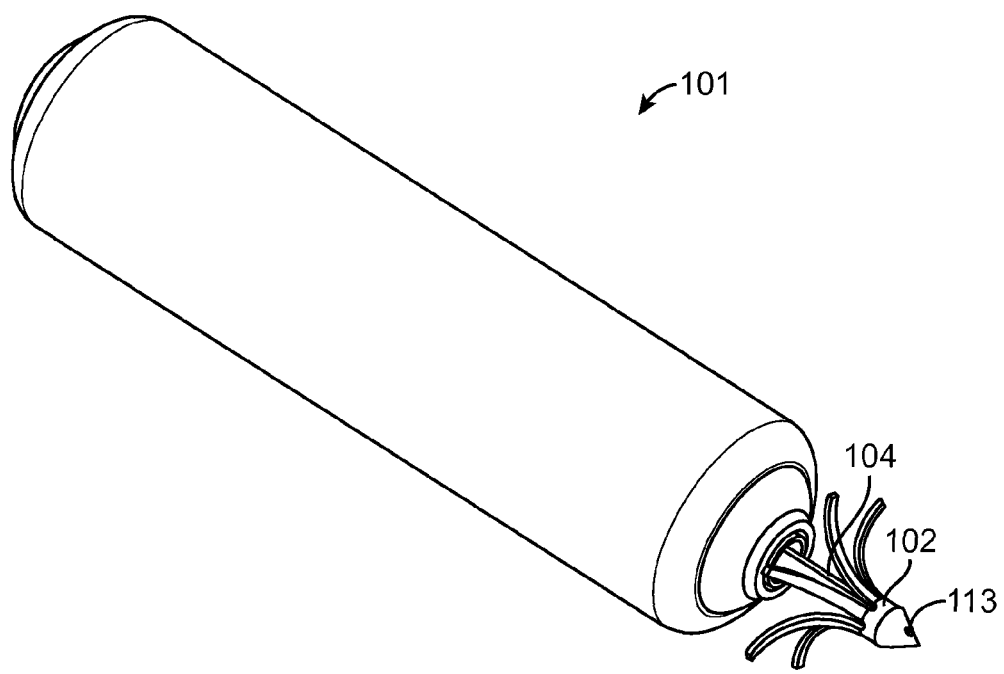
FIG. 1B shows the receiver-stimulator with the anchoring mechanism deployed.
Figure 1C:
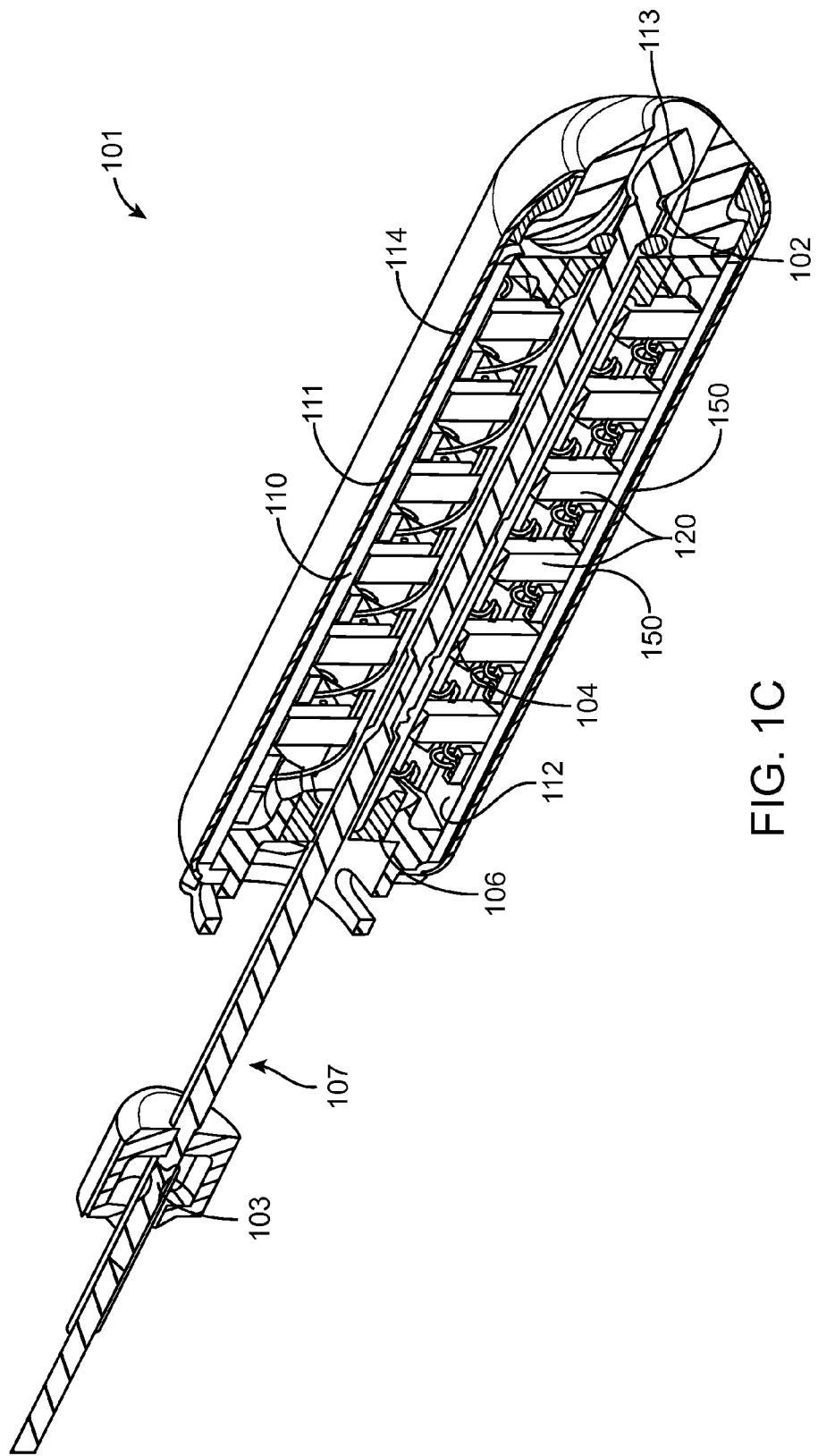
FIG. 1C shows the receiver-stimulator cross-section in the retracted state.
Figure 1D:
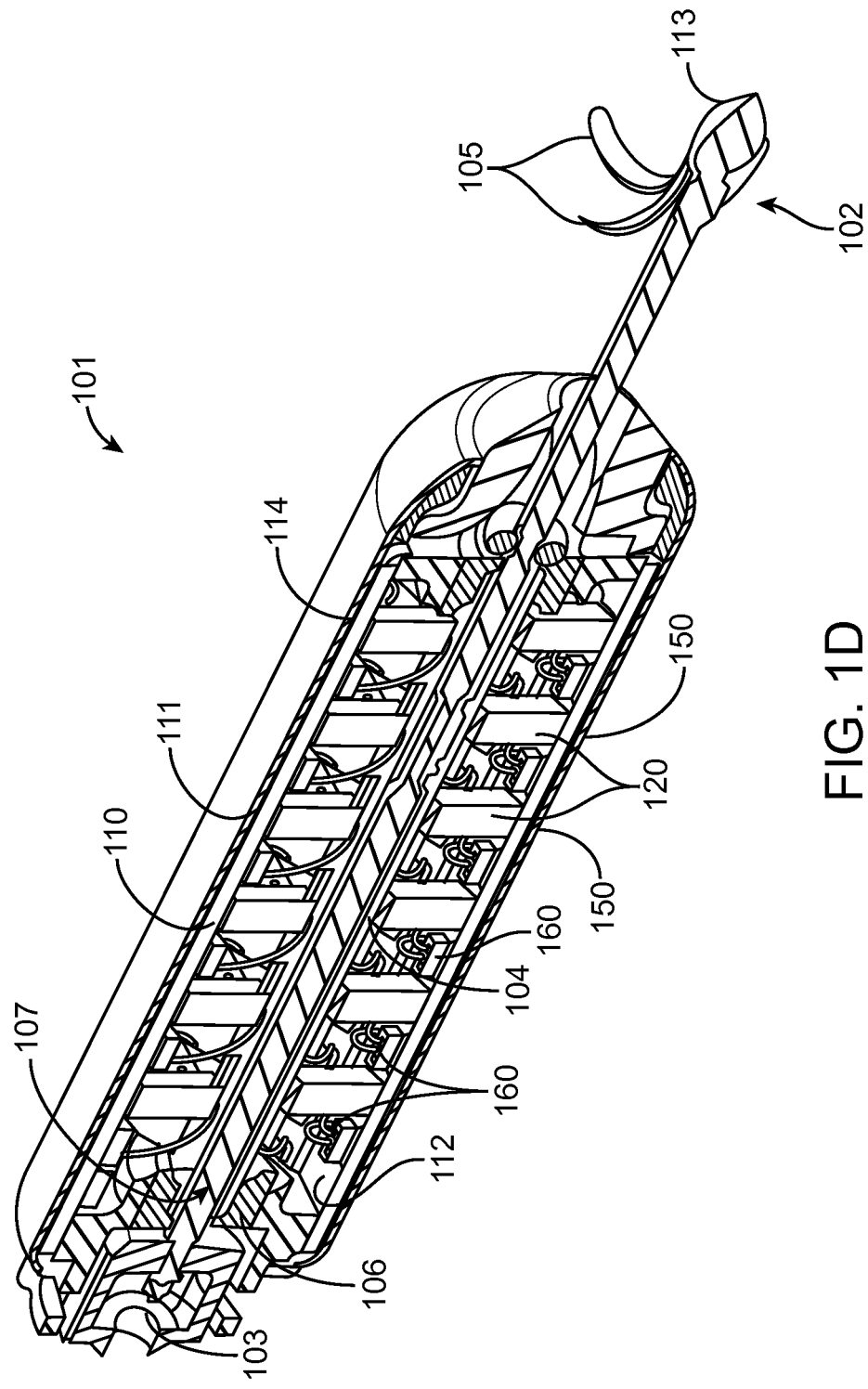
FIG. 1D shows the receiver-stimulator cross-section in the deployed state.

FIGS. 1A-D are diagrams illustrating an implantable receiver-stimulator 101, constructed in accordance with the principles of the present embodiments. FIGS. 1C and 1D are cross-sectional views of the R-S 101 device as shown in FIGS. 1A and 1B, respectively.

The R-S 101 comprises an axle assembly 104 containing a moveable/retractable needle assembly 107 with an anchoring mechanism 102 at its distal end and a detachment mechanism 103 at its proximal end. The anchoring mechanism 102 enables the R-S 101 to be attached to a desired location at the treatment site. The axle assembly 104 comprises an internal cathode feed-through 106 to the needle assembly 107. The needle assembly 107 is configured to move axially in R-S 101 through the axle assembly 104. The proximal end of the R-S 101 may comprise mechanical or electro-mechanical arrangements to engage and disengage the R-S 101 from a delivery catheter.

The needle assembly 107, including the anchoring and detachment mechanisms 102 and 103, is configured to start out in a retracted state as shown in FIGS. 1A and 1C. When the R-S 101 is to be permanently attached to patient tissue, the needle assembly 107 assumes a deployed state as the detachment mechanism 103 is pushed axially forward, for example by a delivery catheter. As shown in FIGS. 1B and 1D, pushing the needle assembly 107 axially forward will insert the anchoring mechanism 102 into patient tissue (delivery catheter not shown).

In the retracted state shown in FIGS. 1A and 1C, the anchoring mechanism 102 is retracted inside the R-S 101 with one or more barbs 105 held in place along the tip of the needle assembly 107, and the detachment mechanism 103 is extended outwards at the proximal end of the R-S 101.

In the deployed state shown in FIGS. 1B and 1D, the anchoring mechanism 102 is pushed distally outwards, allowing its barbs 105 to fan out radially and thereby attach the R-S 101 to patient tissue.

As shown in FIGS. 1C and 1D, the R-S 101 comprises a hermetically sealed enclosure 110. The enclosure 110 has an outer surface 111 and an inner surface 112, constructed using an electrically conductive base, such as titanium, upon which a circuit layer is assembled on the inner surface 112 of the device. In one embodiment, the circuit comprises a thin film ceramic insulating layer and a thin film metal layer. In another embodiment, the circuit is composed of materials having substantially similar acoustic impedances as surrounding materials residing in the acoustic path between the acoustic energy source and the enclosure. Such surrounding materials include patient tissue through which the acoustic waves travel, and elements of the R-S 101 itself.

A plurality of piezoelectric components 120 are affixed to and organized on the inner surface 112 in which an affixed side/face of the piezoelectric component 120 forms an aperture 150 with the wall of the enclosure 110. In response to an acoustic field coupling through the aperture 150 to the piezoelectric component 120, the piezoelectric component 120 converts acoustic power to electrical power. The internal spaces 160 between the piezoelectric components 120 contain materials of low acoustic impedance, such as air, or vacuum making these surfaces non-isotropic. As shown in FIG. 3A, the inner surface 112 further contains a plurality of rectifier circuits 121 each electrically connected to a corresponding piezoelectric component 120. Together, a piezoelectric component, an associated aperture and a rectifier function as a harvesting element.

Figure 6A:
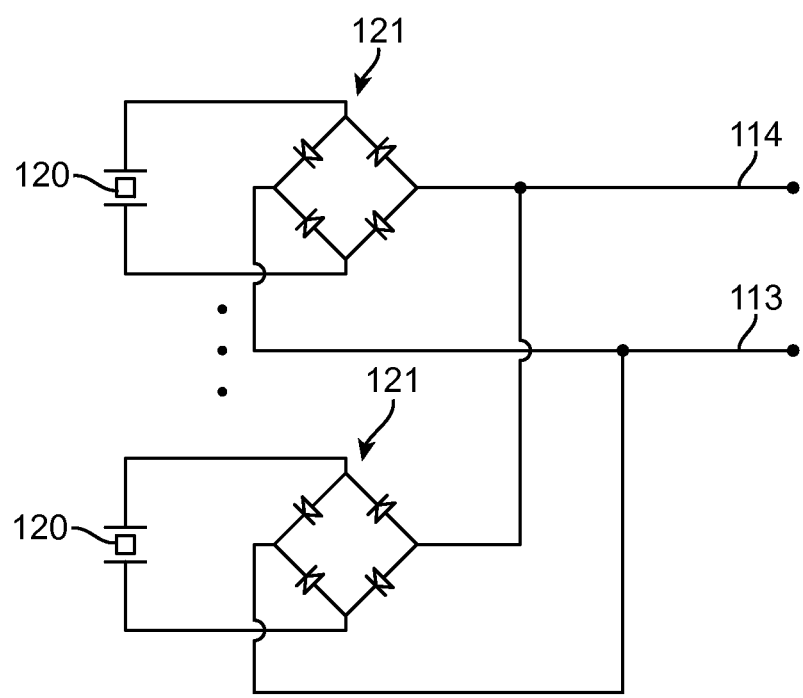
FIG. 6A shows an electrical circuit with harvesting elements connected in parallel.
Figure 6B:
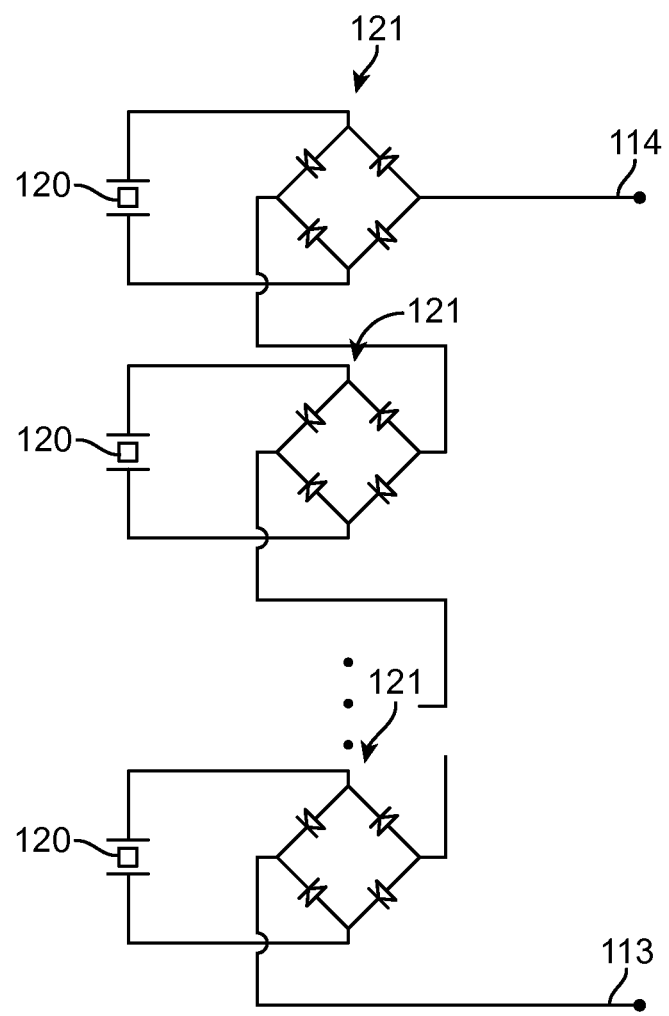
FIG. 6B shows an electrical circuit with harvesting elements connected in series.

In one embodiment, the output of each of the harvesting elements is connected in parallel as illustrated by the abbreviated electrical circuit in FIG. 6A or connected in series as illustrated by the abbreviated electrical circuit in FIG. 6B, and optionally also comprising protection circuitry (not shown) to protect the rectifiers from voltages exceeding a threshold. In one embodiment, such a voltage threshold is approximately 3 to 4 V. In one embodiment, the protection circuitry comprises a Zener diode or a series of GaAs Schottky diodes.

In an embodiment where the stimulation electrodes are of a polarizing type, a direct current (DC) charge can build up on the electrodes unless a discharge path is provided. In traditional pacemakers, the pacing electrodes are shorted using a switch to remove any residual charge on the electrodes when not delivering a stimulus pulse. In embodiments where rectifiers are used to convert an alternating current (AC) signal into a suitable electrical output pulse, there is no discharge path back through the rectifier. Therefore, a discharge path may be provided by using a bleed resistor connected between the stimulation electrodes. Preferably, the bleed resistor is 5-10 times the load impedance in order to provide a sufficient discharge path while not wasting energy that is intended for delivery to the tissue.

In one embodiment, the R-S 101 comprises circuitry to limit the electrical output to the stimulation electrodes in order to prevent the electrical output from exceeding certain currents that would be harmful to the tissue or would have harmful or undesirable side effects for the patient.

While the aperture 150 of a harvesting element is determined in part by the surface area of the piezoelectric component 120 exposed to the acoustic field through the enclosure wall 110, a number of other factors contribute to the effective acoustic aperture, including piezoelectric component dimensions and materials, mechanical properties of the coupling surface of the enclosure 110 wall to which the piezoelectric component is affixed, and proximity of neighboring harvesting elements.

In another consideration for the R-S 101 to attain high efficiency in converting the acoustic field to electrical power, the source impedance of the combined harvesting elements needs to be matched with the load impedance, dictated by the tissue characteristics and the electrical characteristics of the stimulation electrodes. This invention allows matching the impedance of the R-S 101 (source impedance) to the load impedance by a judicious electrical arrangement of the harvesting elements, which could be in series, parallel, or a combination thereof. Another way the source impedance can be manipulated is by changing the dimensions of the individual piezoelectric components 120; for example, changing the cross-section of a piezoelectric component 120 while keeping its height constant changes the impedance of that piezoelectric component.

The inner surface 112 may also contain additional circuitry that connects the output from the harvesting elements to a pair of stimulation electrodes, a cathode 113 and an anode 114 (see FIGS. 1C and 1D). The electrodes are located on the exterior surface of, or otherwise attached to or extended from, the R-S 101 device in electrical contact with the tissue. As described below, in one embodiment, the cathode 113 is part of the tissue engagement mechanism located at the tip of the R-S 101, and the anode 114 is a portion of or the entire exterior surface of the R-S 101. In one embodiment, the R-S 101 device is covered with woven polyester (or other similarly suitable material) to promote tissue in growth.

The R-S 101 is manufactured by attaching and wire bonding a plurality of piezoelectric components 120 and rectifiers 121 to a flat sheet that becomes the enclosure 110 by folding or rolling the sheet to produce an R-S "can" assembly. This assembly process is described below and represented by FIG. 2 and depicted in FIGS. 3A-3D and in an alternative arrangement of components in FIGS. 3E-3I. As can be appreciated any number of arrangements of components can be made. The can assembly 300 (shown in FIG. 3A or alternatively in FIGS. 3E and 3F) is folded to produce an octagonal (or rolled to produce an otherwise substantially cylindrical or tubular) can structure 310, as shown in FIGS. 3C and 3D or alternatively in FIGS. 3G-3I. This process will now be described in more detail.

Figure 2:
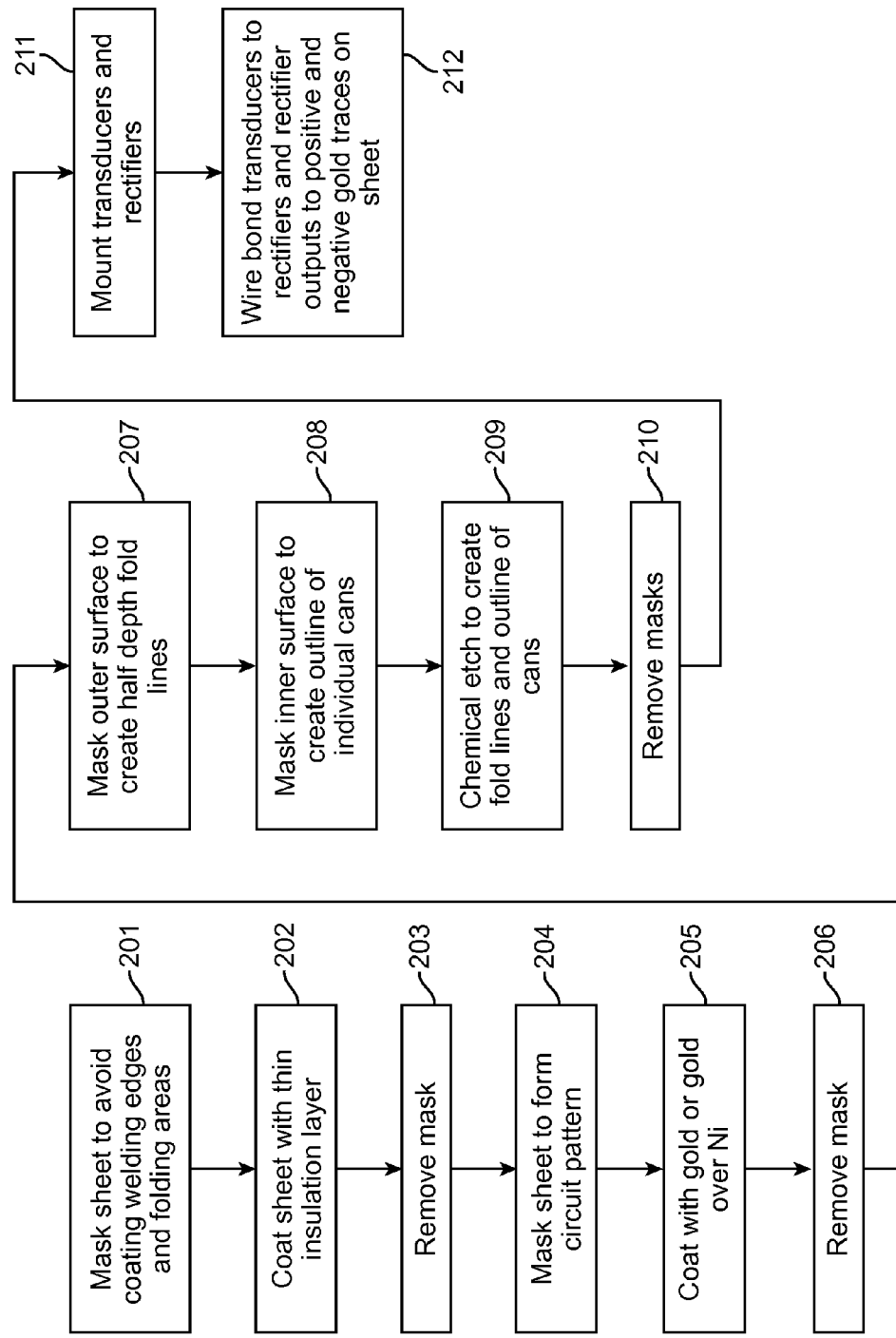
FIG. 2 is a flow diagram illustrating a method for manufacturing a receiver-stimulator.

FIG. 2 is a flow diagram illustrating a method for manufacturing an R-S 101, in accordance with embodiments of the present invention. At step 201, a sheet 301 (see FIG. 3A) is masked to avoid depositing insulation or circuit material onto edges that will later be welded. In one embodiment, the sheet 301 is made of thin titanium. Alternatively, it is contemplated that the sheet 301 may be made of biocompatible material such as low carbon stainless steel, polyimide, polyester, liquid crystal polymer (LCP), or the like, or non-biocompatible material coated with a biocompatible material such as those mentioned above.

Optionally, many sheets 301 can be fabricated out of a larger sheet. In such an embodiment, all the steps described below up to the folding up of the can assembly can be performed on the larger sheet, after which individual can assemblies 300 can be cut from the larger sheet and folded individually.

At step 202, the sheet 301 is coated with a thin electrical insulation layer, such as a very thin ceramic layer. Alternatively, a non-conductive polymer layer such as polyimide can be used instead, or a flexible circuit can be laminated on the sheet 301 to achieve the same results.

At step 203, the mask is removed, and at step 204 the sheet 301 is masked again, this time to form a circuit pattern. At step 205, the masked sheet 301 is coated with a conductive material. It is contemplated that gold or gold over nickel or other such conductive materials will work particularly well, due to their high conductivity and suitability for wire bonding.

At step 206, the mask is removed to reveal the circuit pattern. As shown in FIG. 3 A, the circuit pattern comprises positive and negative conductive traces 302 and 303 which will be connected to the positive and negative outputs of the rectifiers 121. Additional layers of insulator and conductor could be added to form more complex circuitry similar to conventional circuit boards.

At step 207, the sheet 301 is masked to create half depth fold lines by etching. The masking and the fold lines are preferably created on the outer surface 111 of the sheet 301 to avoid interfering with the circuit on the inner surface 112. However, the masking and fold lines can also be created on the inner surface 112 (circuit side), for example, such that they do not interfere with the circuit. Alternatively, circuit traces may be created across the fold lines. Alternatively, the rectifiers could be attached with flip chip connections eliminating a substantial fraction of the wire bonds and simplifying routing.

Additionally, half depth outlines may be etched on either outer or inner surfaces that define locations for the piezoelectric components 120. These outlines also contribute to defining the aperture 150 for a piezoelectric component 120, thereby providing mechanical interruption or isolation, as well as defining an effective aperture which may be larger than the widths of the piezoelectric components 120. Such acoustic apertures 150 may be defined in a number of alternative ways, for example, by etching away (a) surface material that lies outside of the aperture boundaries and leaving material inside of the aperture boundaries unetched, (b) surface material that lies inside of the aperture boundaries and leaving material outside of the aperture boundaries unetched, (c) material at the aperture boundaries (of a certain boundary width) and leaving material inside and outside of the boundaries unetched, or (d) by leaving the aperture boundaries (or a certain boundary width) unetched and etching surface material that lies inside and outside of the aperture boundaries. While such apertures may be etched on the inner surface 112 or the outer surface 111 of the sheet 301, they are preferably etched on the outer surface 111, thereby leaving a smooth surface on the inner surface 112 for attaching the piezoelectric components 120. Alternatively, the surface may be modified by a process other than etching, as known to those of ordinary skill in the art. The masking and etching of fold lines and aperture geometry could also be done before plating with insulator and circuitry layers. Acoustic apertures could also be created by attaching other materials such as frames or cylinders of titanium, ceramic or other material to the substrate in the space not occupied by the piezoelectric components.

At step 208 the inner surface of the sheet 301 is masked to also create outlines of individual can assemblies 300. At step 209, the sheet 301 is chemically etched to create fold lines 304 (as shown in FIG. 3A) and outlines of individual cans. At step 210, the masks are removed, and at step 211 the piezoelectric components 120 and rectifiers 121 are mounted onto the sheet 301. In one embodiment, they are mounted using an adhesive. The bottom electrode coating on the piezoelectric components makes electrical contact with the circuit either by intimate mechanical contact at high points when the adhesive is thin enough, by using an electrically conductive adhesive, by reflowing of indium or tin lead alloys to make the electrical and mechanical connection (similar to conventional surface mounting practice), or by using similar techniques known to those of ordinary skill in the art.

At step 212, the piezoelectric components 120 are wire bonded to their respective rectifiers 121, and the positive and negative outputs of the rectifiers 121 are wire bonded to the positive and negative conductive traces 302 and 303 on the sheet 301. While wire bonding works well due to the minimal influence it has on the resonant structure, other attachment methods, such as tab bonding, flip chip connections, or surface mount technology (SMT) methods would work for other connections made to the piezoelectric components 120 and/or the rectifiers 121.

Figure 3B:
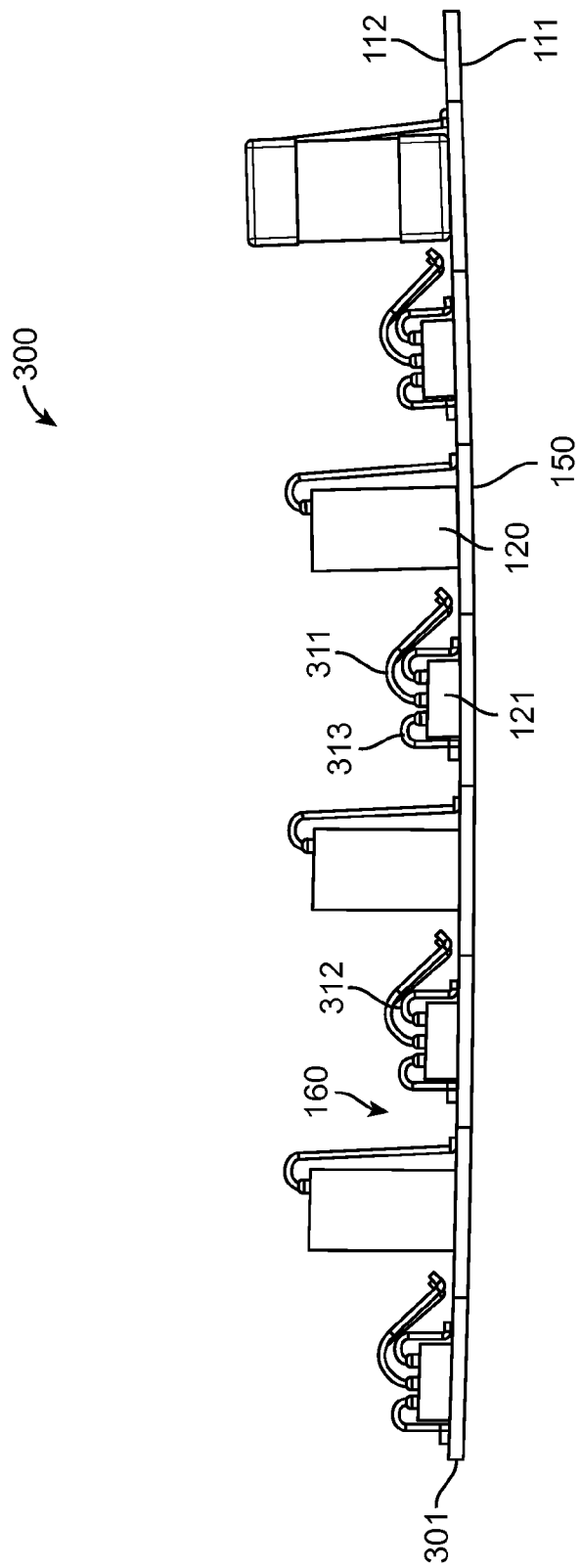
FIG. 3B is a side-view of the can assembly and exemplary piezoelectric components.
Figure 3C:
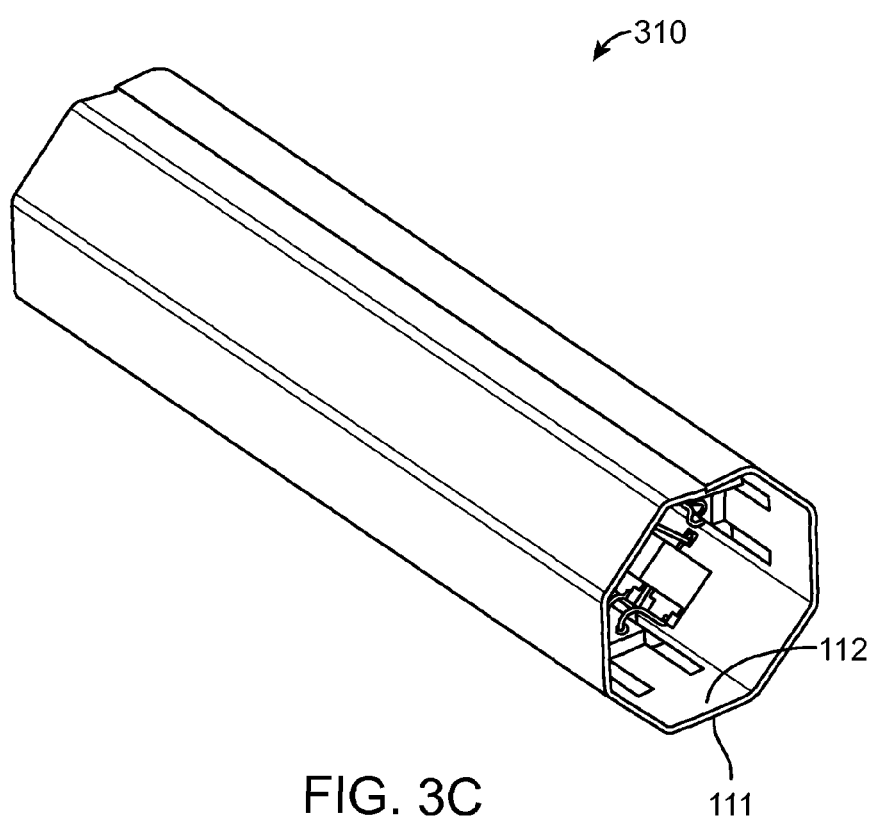
FIG. 3C shows a folded can assembly.
Figure 3D:
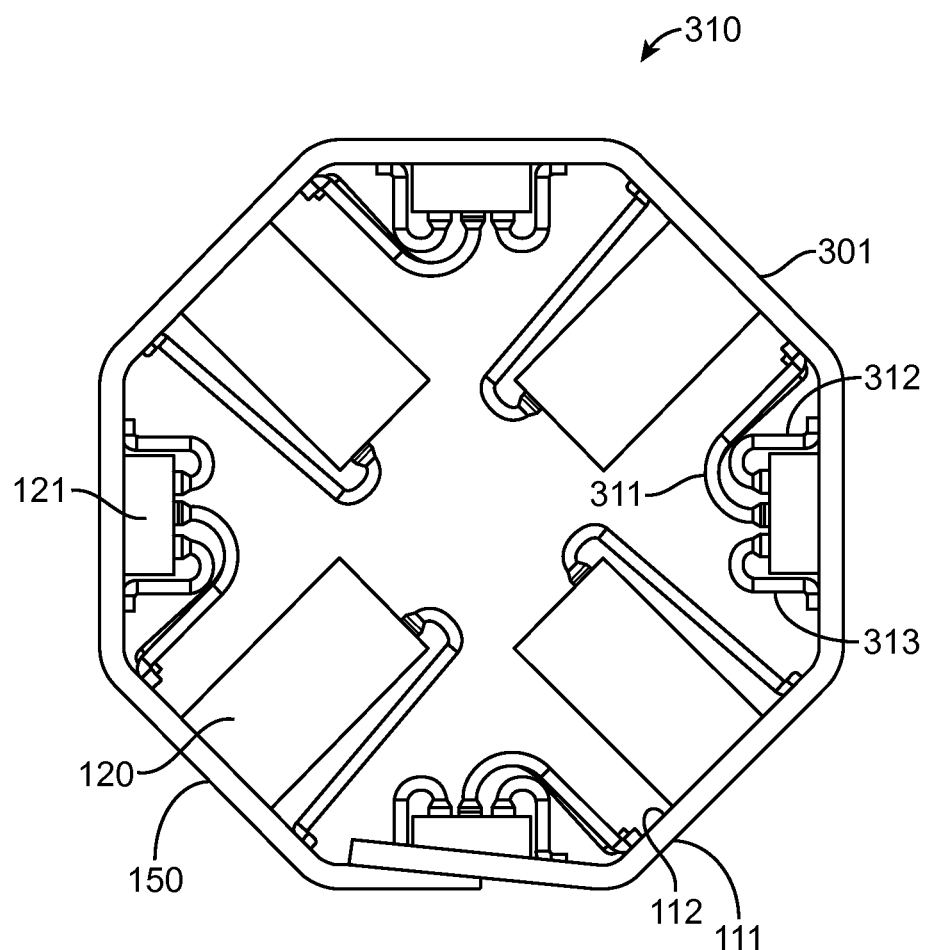
FIG. 3D is a cross-sectional view of the folded can assembly.
Figure 3E:
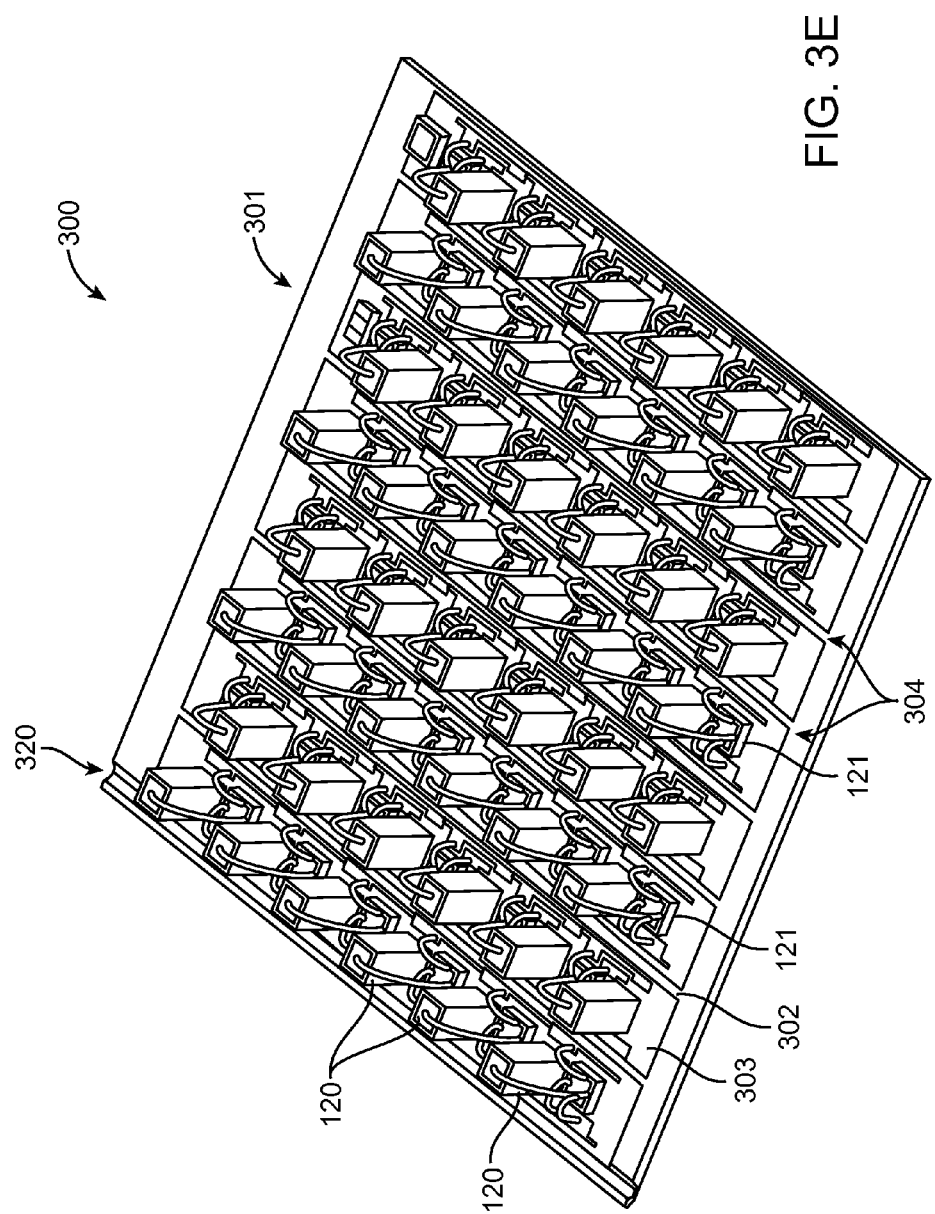
FIGS. 3E-3I show an alternative can assembly with piezoelectric components and rectifiers organized in an exemplary arrangement.
Figure 3F:
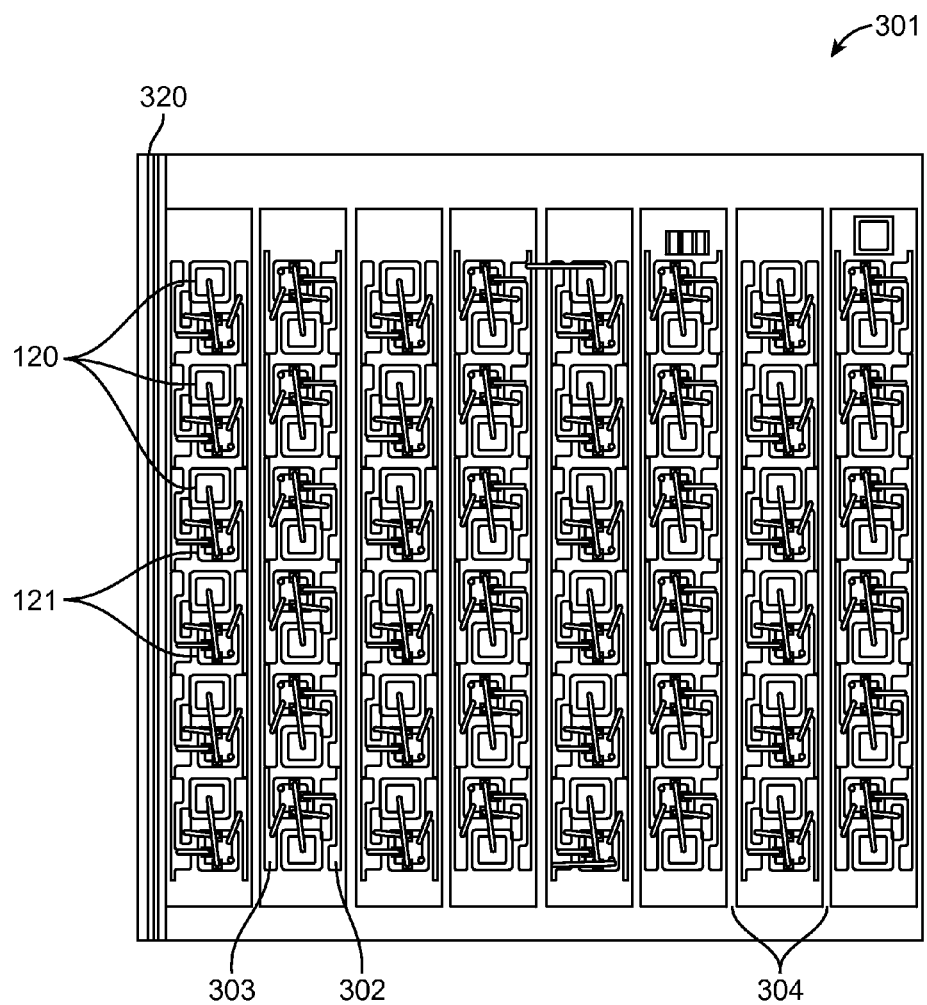

FIG. 3B is a side-view of the flat sheet can assembly 300 of FIG. 3A, showing wire bonds 311 from the inputs of the rectifiers 121 to circuit pads on the sheet 301 which are connected to piezoelectric components 120, wire bonds 312 from the positive outputs of the rectifiers 121 to the positive conductive traces 302 (see FIG. 3A), and wire bonds 313 from the negative outputs of the rectifiers 121 to the negative conductive traces 303 (see FIG. 3A). In the particular exemplary configuration shown, the harvesting elements are connected in parallel. However, any combination of circuit configuration may be obtained by the layout of the circuit mask on the sheet 301, including series or parallel configurations or combinations thereof, as will be obvious to one skilled in the art.

Figure 3G:
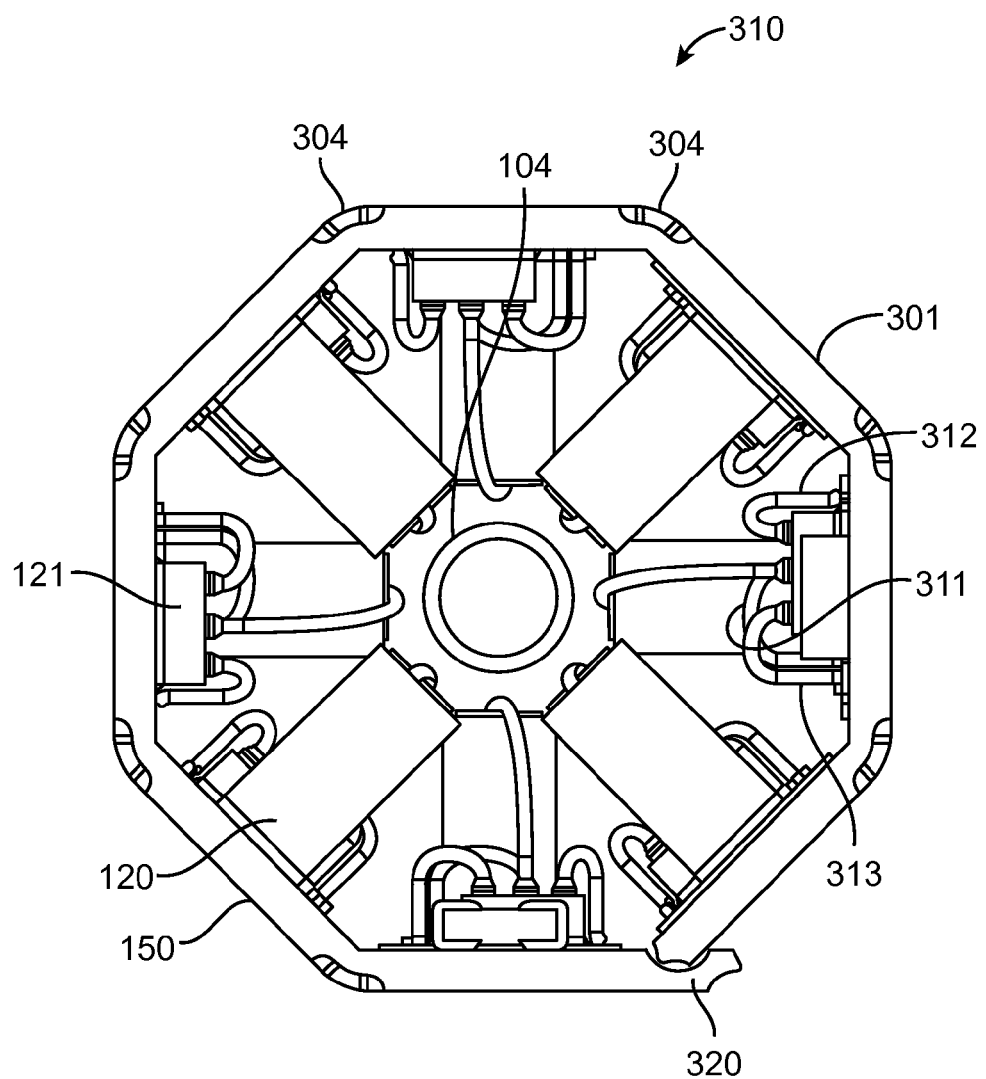
Figure 3H:
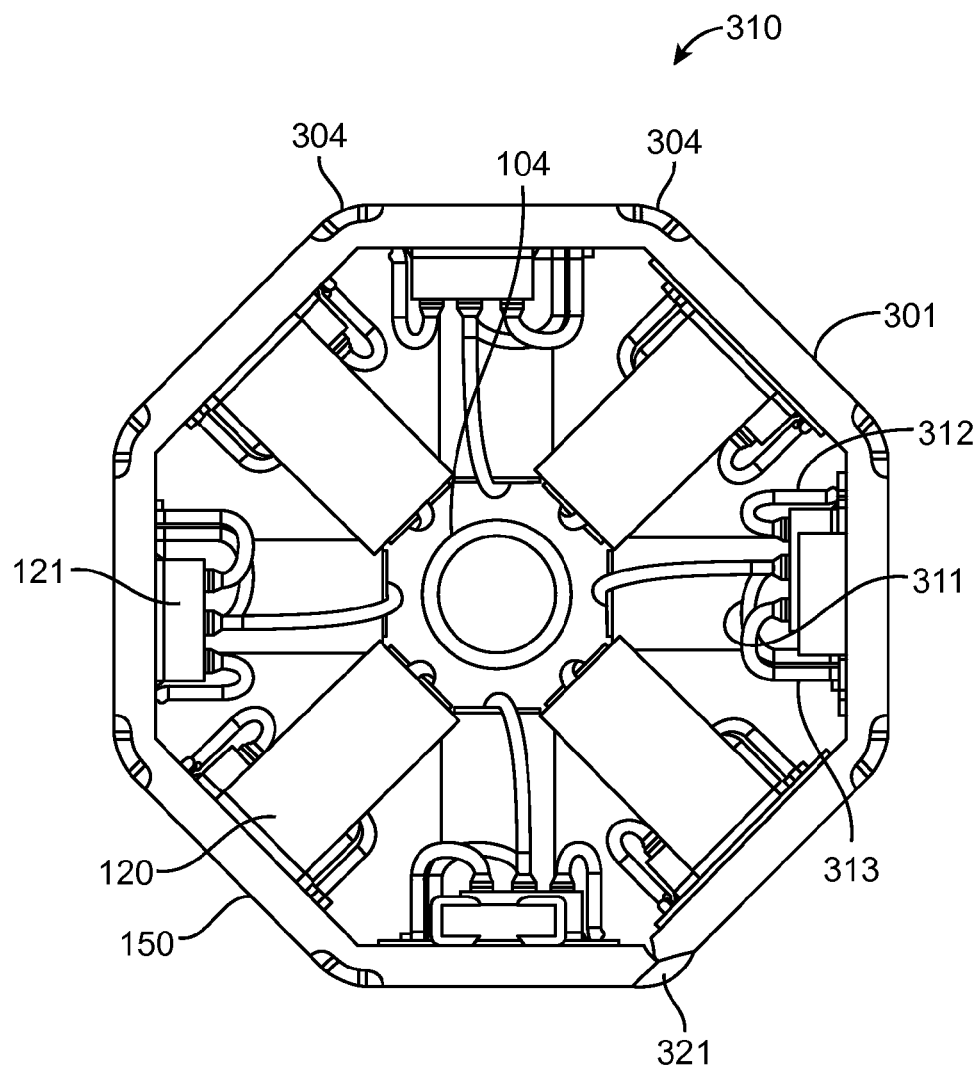
Figure 3I:
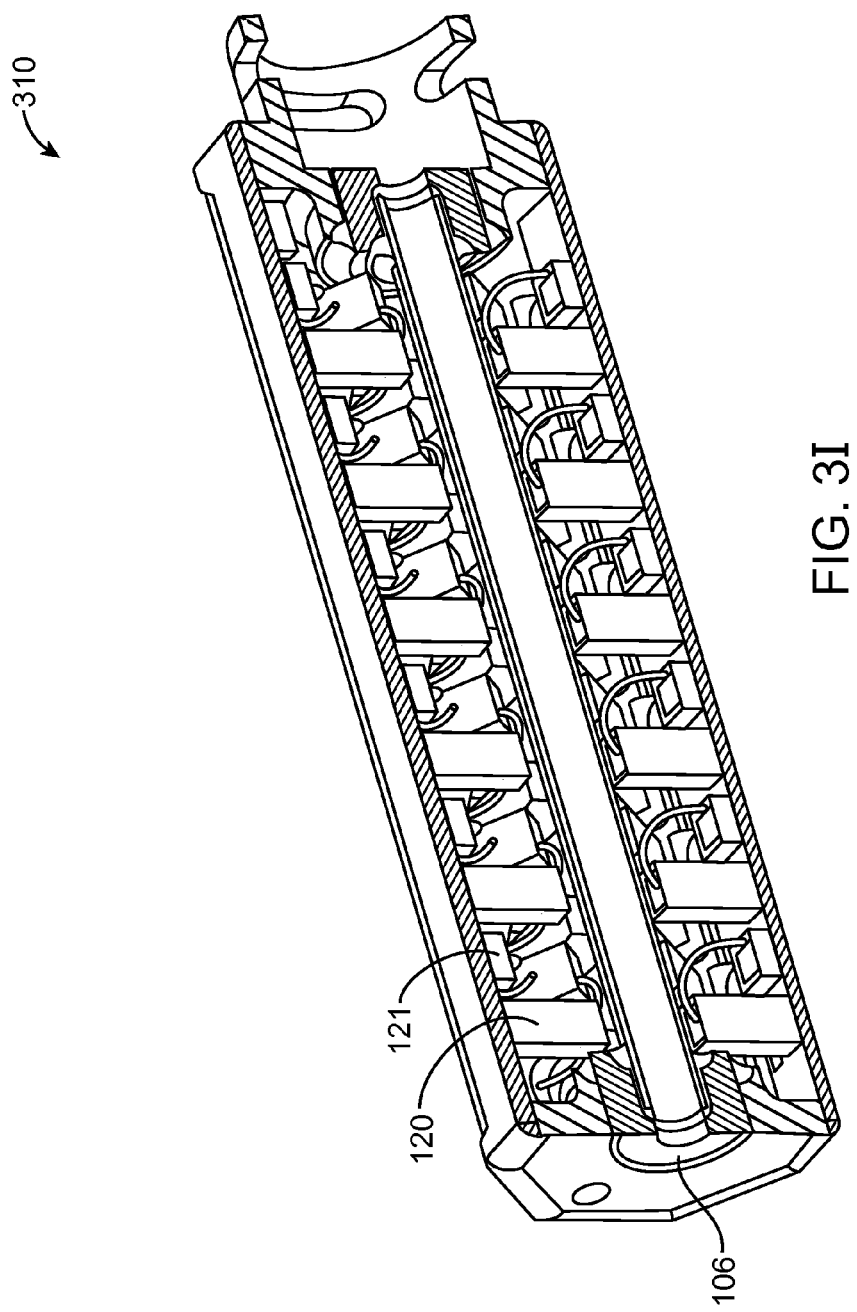

Once the can assembly 300 is complete, it is folded into an octagonal structure or otherwise folded or rolled to a substantially cylindrical can structure 310 as dictated by the fold lines, as shown in FIG. 3C. FIG. 3D is a cross-sectional view of the folded can structure 310 of FIG. 3C showing a compact and an optimal arrangement of the piezoelectric components and the rectifiers. This spatial arrangement allows packing a high number of piezoelectric components into a given volume. The fold lines act to isolate the folding strains away from the attachment points of the piezoelectric components 120 and rectifiers 121. In one embodiment, the can assembly 300 comprises an interlocking joint structure 320 (also known as a "dado joint"), as shown in FIGS. 3A, 3E, 3F, and 3G. This interlocking joint structure 320 helps align the edges of the folded can structure 301 as they are brought together through folding before the edges are welded together. This allows for maximizing the amount of material immediately adjoining the weld, thereby providing for a complete and substantially hole-free seam upon completion of welding. FIG. 3G shows the folded can structure 310 and the interlocking joint structure 320 prior to welding. FIG. 3H shows the welded can structure 310 with a welding seam 321 where the interlocking joint structure 320 provided alignment of the can structure edges.

It is an advantageous aspect that the composite structure of the R-S 101 can operate with a high degree of isotropy even if the individual harvesting elements have a low isotropy. This is due to the diversity of aperture orientations of the harvesting elements. For any given spatial orientation of the R-S 101 relative to the acoustic field, there are harvesting elements whose apertures are oriented such that they are able to harvest a large portion of the acoustic power that is impingent on them. For example, in an R-S 101 with an octagonal cross-section as shown in FIGS. 3C and 3D, there are four differently oriented harvesting elements, each contributing a potentially different energy output, but in aggregate contributing to a substantially constant overall power output of the R-S 101 as the direction of the incoming acoustic field is varied.

In one embodiment, the electrical output of the rectifiers 121 is used to directly stimulate tissue. In an alternative embodiment, the R-S 101 further comprises processing circuitry that manipulates the electrical output converted by the rectifiers 121 to produce an electrical signal that stimulates tissue. The processing circuitry manipulates the electrical output such that it is suitable for the particular stimulation application at hand, such as cardiac pacing, nerve stimulation, brain stimulation, voluntary muscle stimulation, pain amelioration, or the like. Such manipulation may involve summing or conditioning the electrical signals from the individual rectifiers 121 to produce the biologically stimulating electrical output.

As described above, the R-S 101 further comprises at least two electrodes to stimulate patient tissue: a cathode 113 and an anode 114. The cathode 113 and anode 114 are electrically connected as illustrated in the abbreviated electrical circuits of FIG. 6A or 6B to negative and positive outputs of the rectifiers 121 (or of the processing circuitry, in embodiments where such circuitry is used in the R-S 101). Either or both of the electrodes 113 and 114 may be mounted on the exterior surface of, or otherwise attached to the R-S 101, in some instances forming a portion of the device enclosure.

In the exemplary embodiments shown in FIGS. 1A-1D, the cathode 113 is disposed on the needle assembly 107 and is routed through a feed-through 106 in the axle assembly 104 at the distal tip of the R-S 101. FIG. 1C shows the tip of the cathode 113 exposed at the distal tip of the axle assembly 104, and the body of the cathode 113 extending through the axle assembly 104 and into the R-S 101 to electrically connect with a flexible conductive coil 115 that is connected to the negative output of the rectifiers 121 (the connection between the conductive coil 115 and rectifiers 121 not shown). FIG. 1D shows the flexible conductive coil 115 stretched as the axle assembly 104 is pushed axially forward, maintaining an electrical connection between the cathode 113 and the negative output of the rectifiers 121 or electrical signal processing circuitry. In embodiments where a processing circuitry is used, the conductive coil 115 is connected to the negative output of the processing circuitry. The anode 114 is represented by a portion of the device enclosure and extends into the R-S 101 to electrically connect with the positive output of the rectifiers 121 electrical signal processing circuitry (this internal connection is not shown).

According to the present embodiments, the length of the R-S 101 is preferably about 4-12 mm, more preferably about 6-10 mm, and most preferably about 8 mm; the diameter of the R-S 101 is preferably about 3-16 French (1.0 to 5.3 mm), more preferably about 5-12 French (1.7 to 4.0 mm), and most preferably about 6-8 French (2.0 to 2.7 mm); the operating frequency of the R-S 101 is preferably about 200 kHz-3 MHz, more preferably about 600 kHz-1.8 MHz, and most preferably about 950 kHz-1.2 MHz; and the number of harvesting elements in the R-S 101 is preferably about 6-200, more preferably about 30-100, and most preferably about 40-60.

As described above, the implantable R-S 101 devices of the present embodiments are also capable of functioning at a high degree of isotropy. This means that the composite structure of the R-S 101 device produces output electric power that is constant or nearly constant as the relative orientation of the R-S 101 to the acoustic source is varied. It is contemplated that the electric power produced by the R-S 101 device and delivered to the tissue in proportion to the incident acoustic intensity impinging on the R-S 101 will be such that the minimum effective area preferably is no more than −6 dB, more preferably is no more than −3 dB, and most preferably no more than −1 dB from the maximum effective area as the orientation of the receiver-stimulator varies relative to that of the acoustic source.

The R-S 101 assembly may comprise one or more piezoelectric components 120 in the shape of a cuboid, a post, a cylinder, or a structure with a hexagonal construction or the like, having a pair of transducer electrodes formed over opposed surfaces thereof. The cuboid is a preferred embodiment, since a structure with a square or rectangular cross-section is easy to manufacture. Additionally, a cuboid shape satisfies the requirement of being able to pack the most number of piezoelectric components 120 into a given volume. In a first exemplary embodiment, the piezoelectric component 120 may be composed of a single-crystal or polycrystalline ceramic piezoelectric material. In a preferred mode, the piezoelectric components operate in resonance, and more preferably in a thickness mode resonance. Also in a preferred embodiment, the natural structural resonance of the R-S 101 body will overlap the resonance of the transducer. One advantage of using single-crystal piezoelectric material is that the piezoelectric components can be smaller compared to using polycrystalline ceramic piezoelectric material, due to the lower velocity of sound in single-crystal piezoelectric materials. When the piezoelectric material is formed in the shape of a cuboid, the opposed transducer electrodes may typically be formed over the two opposing square surfaces of the piezoelectric component, although transducer electrodes over the other surfaces may also be used.

In a still further embodiment of the implantable R-S 101 of the present invention, the R-S 101 comprises a plurality of individual harvesting elements containing piezoelectric components 120, which themselves will typically have a maximum dimension that is approximately one-half wavelength of the expected acoustic wave frequency, but the cumulative lateral dimensions of the R-S 101 will preferably be much greater than a single wavelength.

The harvesting elements 120 in the can structure 310 have apertures which are arranged substantially orthogonal to the longitudinal axis of the can structure 310. The least favorable direction of the propagation of acoustic energy is when the energy propagates substantially parallel to this longitudinal axis. Therefore, in an optional embodiment, the R-S 101 further comprises a plurality of end cap harvesting elements 120 which are organized such that their apertures are substantially orthogonal to the long axis of the can structure 310. This orthogonal arrangement allows the combined output of the plurality of harvesting elements of the R-S 101 to maintain a more constant output power when the acoustic energy propagates substantially parallel to the longitudinal axis of the can structure 310.

Figure 4A:
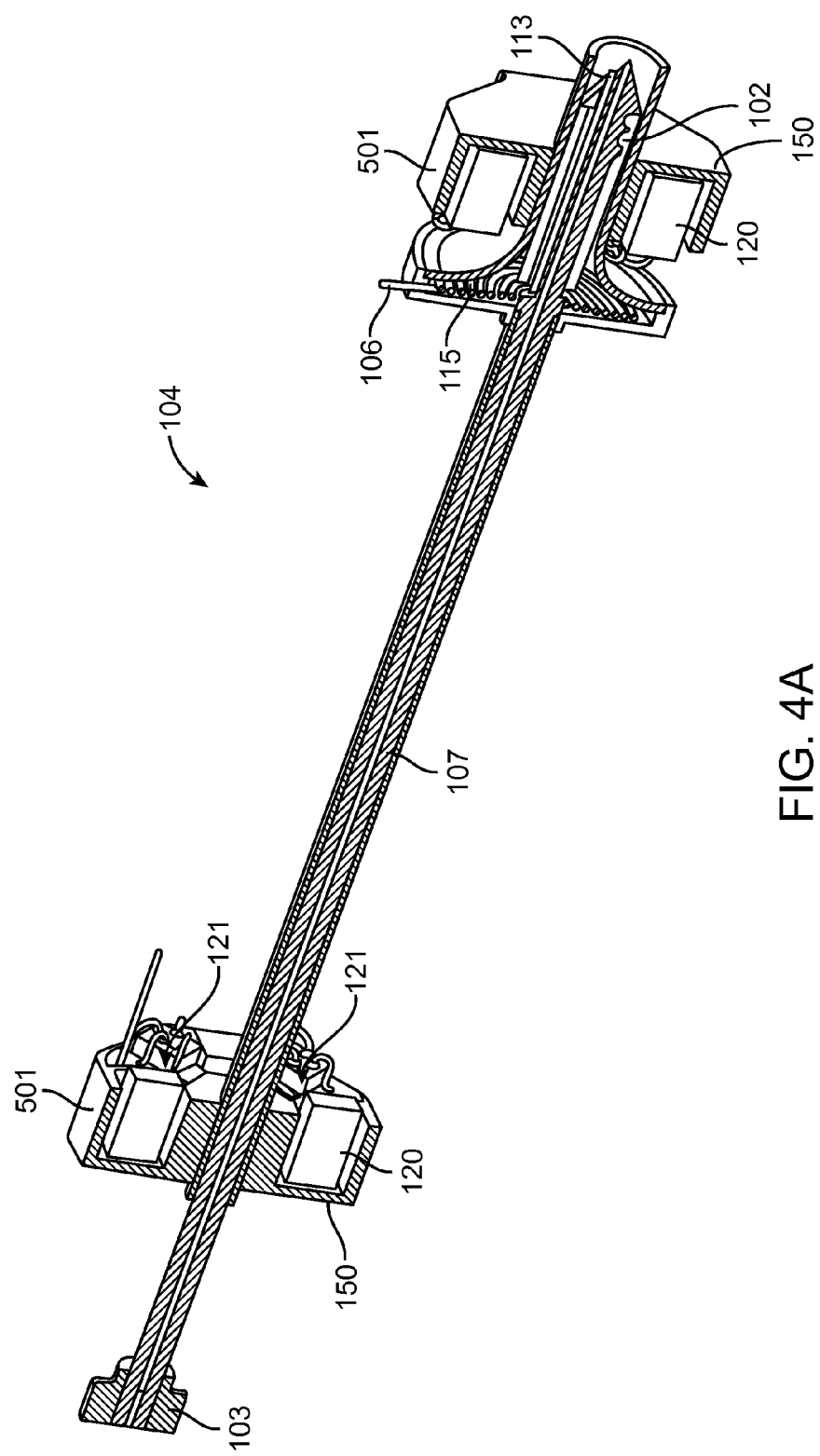
FIG. 4A shows a partial receiver-stimulator assembly with two end caps and an axle assembly.

FIG. 4A is a cross-sectional illustration of an exemplary embodiment of an axle assembly 104 with end caps. The axle assembly 104 has an end cap 501 at the proximal end and another end cap 501 at the distal end. The end caps 501 comprise harvesting elements whose apertures 150 are arranged orthogonal to the apertures of harvesting elements 120 on the sides of the can structure 310 described above. The can structure 310 is not shown in FIG. 4A in order to more clearly illustrate the end caps 501. The can structure 310 would be placed between the end caps 501.

Figure 4B:
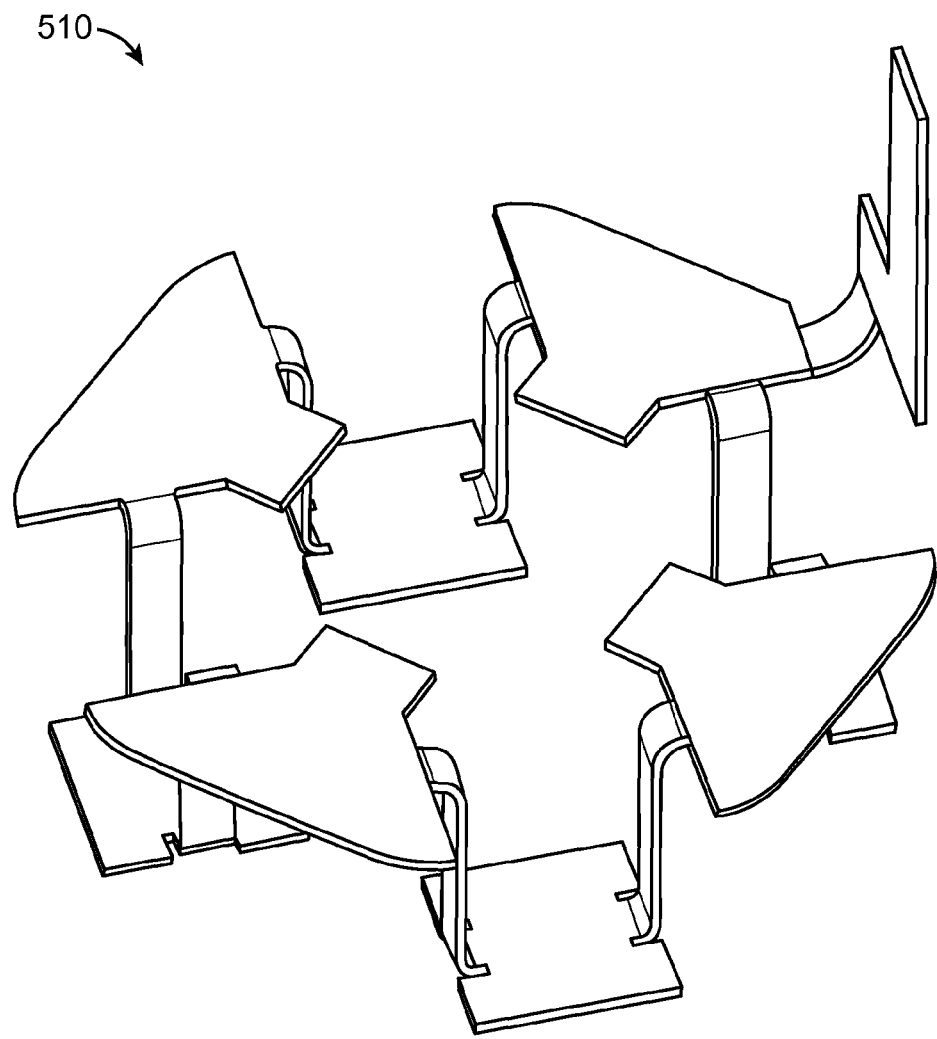
FIG. 4B shows a polyimide, polyester, or liquid crystal polymer (LCP) flex circuit for the end cap.
Figure 4C:
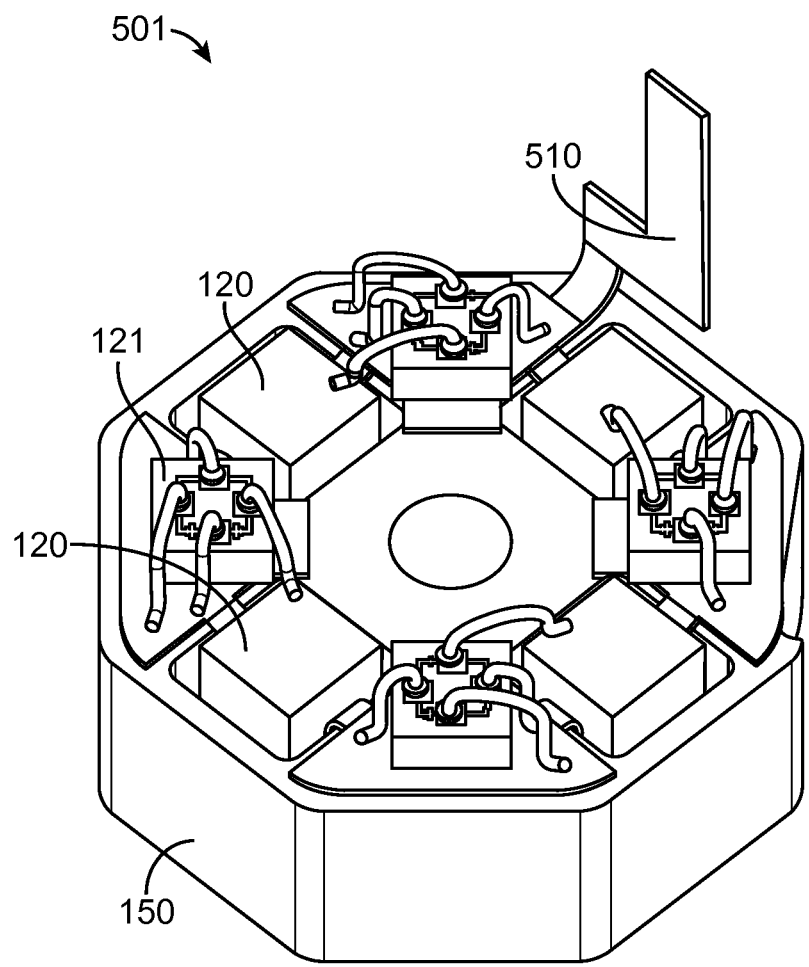
FIG. 4C shows an end cap assembly.
Figure 4D:
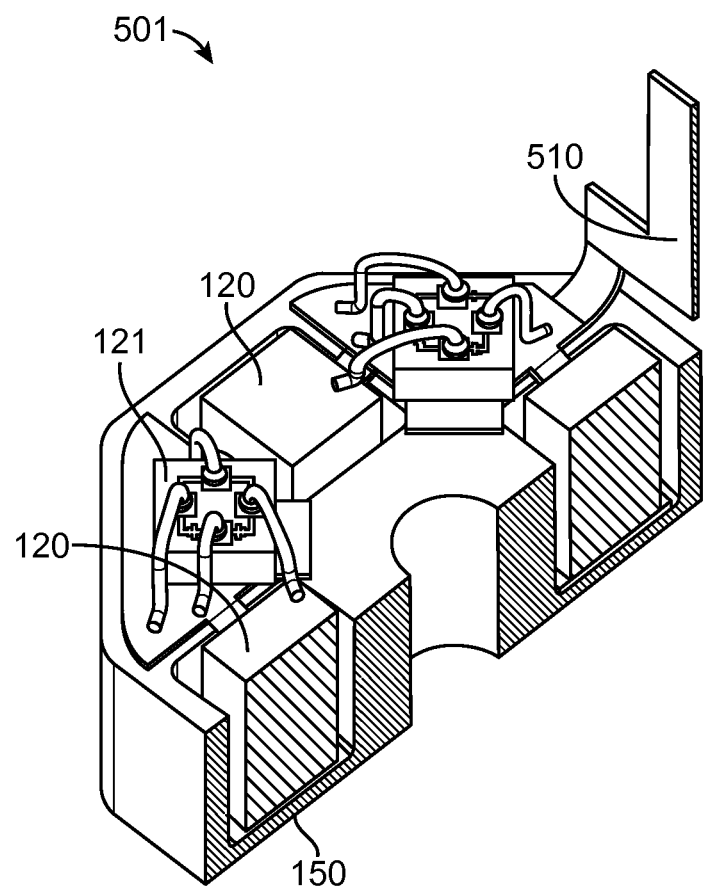
FIG. 4D is a cross-sectional view of an end cap assembly.
Figures 5A, 5B:
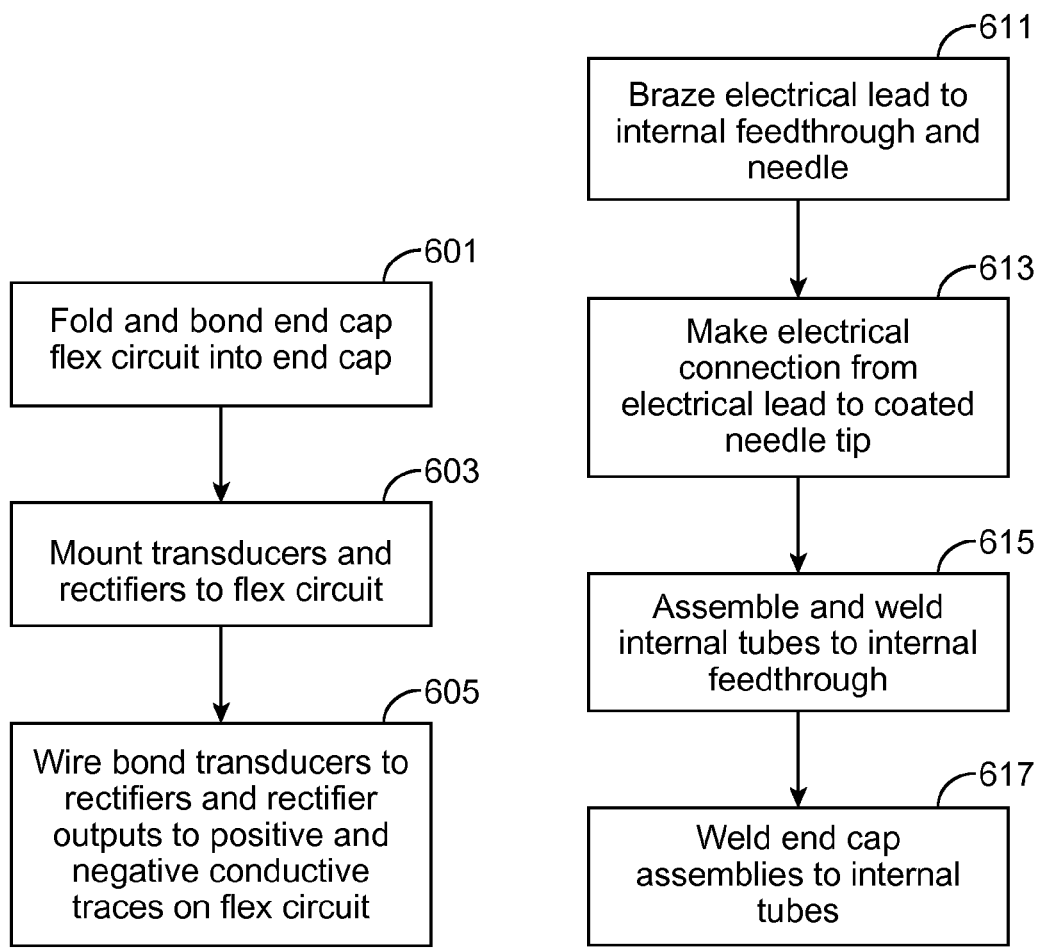
FIG. 5A is a flow diagram illustrating a method for assembling an end cap.
FIG. 5B is a flow diagram illustrating a method for assembling an axle assembly.

FIG. 5A is a flow diagram illustrating a method for assembling an end cap 501, in accordance with an embodiment of the present invention. At step 601, an end cap flex circuit 510 is folded and bonded into an end cap structure. FIG. 4B shows an exemplary end cap flex circuit 510. At step 603, a plurality of piezoelectric components 120 and rectifiers 121 are bonded to the flex circuit 510, as shown in FIG. 4C and in the cross-section view of FIG. 4D. At step 605, the piezoelectric components 120 are wire bonded to their respective rectifiers 121, and the positive and negative outputs of the rectifiers 121 are wire bonded to positive and negative conductive traces on the end cap flex circuit 510 (similar to the positive and negative conductive traces of the can assembly 300, as described above).

FIG. 5B is a flow diagram illustrating a method for assembling an axle assembly 104, in accordance with an embodiment of the present invention. At step 611, an electrical lead (serving as the cathode 113) is brazed to the internal cathode feed-through 106 of the axle assembly 104. The axle assembly 104 is coated with a conductive material at its distal tip, and at step 613 an electrical connection is made from the electrical lead 113 to the coated axle assembly 104 tip. At step 615, one or more internal tubes are assembled and welded to the internal cathode feed-through 106. The internal tubes complete the hermetic enclosure while allowing a through hole for the axle assembly 104 to pass and be deployed. At step 617, the end cap assemblies 501 are welded to the internal tubes.

In a another aspect of the present invention, methods for transmitting an acoustic field to an implanted R-S 101 comprise implanting an R-S 101, typically formed as an assembly of multiple harvesting elements, the R-S 101 having a high degree of isotropy as described above in connection with the devices of the present invention; directing an acoustic field to the implanted R-S 101 from an acoustic source, which may be implanted or located externally, to focus or maximize the acoustic field on the R-S 101; using the harvesting elements that are exposed to the acoustic field through their aperture 150 to transfer acoustic power to their associated piezoelectric components 120 which in turn convert the acoustic power to create electrical power; using the rectifiers 121 to produce an electrical output from the electrical power that is delivered to stimulation electrodes in electrical contact with tissue; and transmitting the acoustic field for sufficient time to produce sufficient electrical energy to stimulate the tissue. The electrical energy flowing between the stimulation electrodes of the R-S 101 may possess specific characteristics of voltage, current, waveform, and the like. These electrical characteristics will be selected to stimulate the target cardiac tissue, nerve tissue, brain tissue, voluntary muscle tissue, bone tissue, or the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for manufacturing an implantable receiver-stimulator for converting an acoustic field to electrical power comprising the steps of:
    forming an insulating layer on an electrically conductive sheet;
    forming a circuit pattern on the insulating layer; electrically connecting a first plurality of acoustic piezoelectric components to the circuit pattern on the sheet;
    electrically connecting a plurality of individual rectifier circuits to the circuit pattern on the sheet, the rectifier circuits configured to convert electrical power output from the piezoelectric components to a biologically stimulating electrical output;
    electrically connecting the biologically stimulating electrical output to a pair of stimulation electrodes; and folding the sheet into an octagonal or otherwise substantially cylindrical can structure, thereby arranging the acoustic piezoelectric components such that acoustic energy is harvested efficiently from any direction of the propagating acoustic field.

2. The method of claim 1, wherein the acoustic piezoelectric components are composed of a piezoelectric material, optionally wherein the piezoelectric material is one of a poly crystalline ceramic piezoelectric material or a single crystal piezoelectric material.

3. The method of claim 2, wherein the piezoelectric components are in the shape of a cuboid, wherein one of the faces of the cuboid is mounted to the circuit pattern on the sheet.

4. The method of claim 1, wherein the rectifier circuitry comprises one or more rectifiers connected in parallel and protection circuitry to protect the rectifiers from damage due to voltages above approximately 4V.

5. The method of claim 4, wherein the protection circuitry comprises a Zener diode or a series of GaAs Schottky diodes.

6. The method of claim 1, further comprising: affixing an end cap to the can structure, the end cap having a second plurality of acoustic piezoelectric components composed of a piezoelectric material, wherein the second plurality of piezoelectric components has a piezoelectric axis that is substantially perpendicular to that of the first plurality of piezoelectric components.

* * * * *